United States Patent [19]

Bernhardt et al.

[11] Patent Number: 4,946,977
[45] Date of Patent: Aug. 7, 1990

[54] METHOD FOR THE PREPARATION OF ORGANOSILANES CONTAINING METHACRYLOXY OR ACRYLOXY GROUPS

[75] Inventors: Günther Bernhardt, Sankt Augustin; Jürgen Amort, Troisdorf; Margret Haas, Cologne; Horst Hanisch, Hennef; Heinz Kragl, Troisdorf, all of Fed. Rep. of Germany

[73] Assignee: Huels Troisdorf AG, Cologne, Fed. Rep. of Germany

[21] Appl. No.: 246,317

[22] Filed: Sep. 19, 1988

[30] Foreign Application Priority Data

Sep. 25, 1987 [DE] Fed. Rep. of Germany ....... 3732356

[51] Int. Cl.$^5$ ............................. C97F 7/08; C97F 7/18
[52] U.S. Cl. .................................................... 556/440
[58] Field of Search ........................................ 556/440

[56] References Cited

U.S. PATENT DOCUMENTS

| | | | |
|---|---|---|---|
| 2,550,205 | 4/1951 | Speier | 556/440 |
| 2,582,568 | 1/1952 | Speier | 556/440 |
| 2,956,044 | 10/1960 | Merker | 556/440 |
| 3,258,477 | 6/1966 | Plueddemann et al. | 556/440 |
| 3,878,263 | 4/1975 | Martin | 556/440 X |
| 4,478,990 | 10/1984 | Kohns et al. | 556/440 X |
| 4,568,260 | 2/1986 | Ballenkamp et al. | 556/440 |

*Primary Examiner*—Paul F. Shaver
*Attorney, Agent, or Firm*—Felfe & Lynch

[57] ABSTRACT

The present invention is in the preparation of methacrylic or acryloxyalkylalkoxysilanes by the reaction at a temperature of from 80° and 130° C. of an alkali (meth) acrylate with a halogen alkylalkoxysilane in the presence of a quaternary ammonium salt which has long-chin alkyl moieties, in which the sum of all carbon atoms is between 10 and 40 as a phase-transfer catalyst. In the new procedure no solvents need to be used. The yields are better than 95%.

15 Claims, No Drawings

METHOD FOR THE PREPARATION OF ORGANOSILANES CONTAINING METHACRYLOXY OR ACRYLOXY GROUPS

BACKGROUND OF THE INVENTION

The present invention is in a method for the preparation of organosilanes containing methacryloxy or acryloxy groups, which are also referred to hereinafter as acrylosilanes. The method is based on the known reaction of alkali methacrylates or alkali acrylates with chloroalkylsilanes in the presence of quaternary ammonium salts as catalysts.

Japanese patent application 51348/65 discloses that acrylosilanes of the general formula

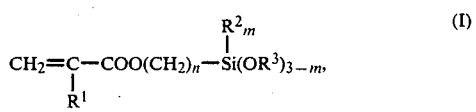

in which $R^1$ represents a hydrogen atom or a methyl moiety, $R^2$ an alkyl moiety with 1 to 4 carbon atoms, $R^3$ alkyl groups with 1 to 4 carbon atoms, m either 0 or 1 or 2, and n a number from 1 to 4, can be prepared by the reaction of solid alkali salts of methacrylic acid or acrylic acid with chloroalkylsilanes of the general formula

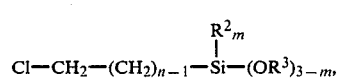

in which $R^2$ and $R^3 = C_1$ to $C_4$ alkyl groups, m=0 to 2, and n=1 to 4, in the presence of quaternary ammonium salts as solid-fluid phase transfer catalysts.

Triethylamine, dimethylaniline, tetramethyl ammonium chloride and benzyltrimethyl ammonium chloride are named in the Japanese application as phase transfer catalysts. Both of the last-named compounds are used in the examples given in the Japanese patent application for the reaction between the solid phase, consisting of the alkali salt of the methacrylic or acrylic acid, and the liquid phase, consisting of the chloroalkylsilane and the phase transfer catalysts.

High reaction temperatures of 140° C to 180° C are necessary for the performance of the reaction when using the above catalysts. The reaction times can extend up to 6 hours. Moreover, a large excess of chloroalkylsilane, which can amount to 10 times the molar amount of alkali methacrylate or acrylate, is required. Furthermore, additional solvent, such as dimethylformamide, toluene or xylene, must be added.

The organosilane yields in this known method are decidedly less than 90% and often amount to only about 70%. When a molar ratio of alkali (meth)acrylate to chloroalkylsilane is 1:1, the yield is only 65% and the formation of a large amount of polymeric material accompanies the product.

Furthermore, the required high reaction temperatures, the large excesses of chloroalkylsilanes, the additional solvent, and the long reaction times, are all decided disadvantages. High temperatures promote the formation of undesired polymeric products. Long reaction times and large excesses of chlorosilane lead to a considerable reduction of the yield per unit of space and time. Furthermore, the large excesses of chloroalkylsilane and the use of an additional solvent adversely affects the energy balance in the purification of the organosilanes by distillation. Also, the use of an additional solvent adversely affects the yield of the organosilanes.

The problem therefore existed of conducting the reaction between alkali (meth)acrylates and chloroalkylsilanes with the formation of acrylosilanes such that it would be possible to operate at low reaction temperatures, obtain a higher yield per unit of space and time, and minimize the percentage of polymeric products.

SUMMARY OF THE INVENTION

For the solution of this problem a method has been found for the preparation of acrylosilanes of the general formula I:

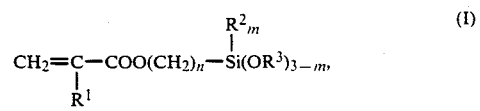

in which $R^1$ represents a hydrogen atom or a methyl moiety, $R^2$ an alkyl moiety of 1 to 4 carbon atoms, $R^3$ alkyl groups with 1 to 4 carbon atoms or alkoxyalkyl groups with a total of 2 to 4 carbon atoms, m represents 0 or 1 or 2, and n represents 1 or 3 or 4, by the reaction of alkali salts of methacrylic acid or acrylic acid with halogen alkylsilanes of the general formula II:

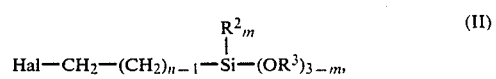

in which $R^2$, $R^3$, m and n are defined as above, in the presence of a phase transfer catalyst being a quaternary ammonium salt of the general formula III:

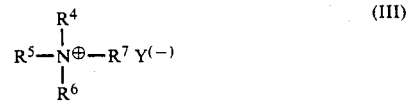

in which $R^4$ to $R^7$ are identical or different alkyl moieties with 1 to 37 carbon atoms, the sum of all carbon atoms amounting to from 10 to 40, and $Y^{(-)}$ represents a chloride, bromide, sulfate or phosphate ion, and the reaction is performed at a temperature of from 80° C. to 130° C.

In the above-described method of the invention, it is possible to operate at considerably lower temperatures than in the method described in the Japanese patent application, and still obtain yields which are far greater than in the known method. A special feature of the method of the invention is that the formation of polymeric products is extremely low.

The quaternary ammonium salts suitable for use in the invention are those which correspond to the above Formula III. The following are examples: tributyl methyl ammonium chloride, triethylcetyl ammonium bromide, didodecyl dimethyl ammonium chloride, distearyl dimethyl ammonium chloride, tricaprylmethyl ammonium chloride, ALIQUAT$^{(R)}$ 336 (tris(n-C$_8$- and C$_{10}$-alkyl)methyl ammonium chloride), trioctyl methyl ammonium chloride, or tetrabutyl ammonium chloride or bromide.

From this list it is apparent that those quaternary ammonium salts are also suitable as catalysts whose alkyl substituents have unequal chain lengths and can also consist of a mixture of different alkyl groups.

Trioctyl methyl ammonium chloride, tetrabutyl ammonium chloride or bromide, and ALIQUAT$^{(R)}$ 336 are especially preferred.

The speed of the reaction of alkali salts of methacrylic acid or acrylic acid with halogen alkyl silanes of the general Formula II is considerably accelerated in comparison to the known methods by the use of the quaternary ammonium salts as catalysts, while at the same time the reaction temperature is lowered and the required react time is decreased, The reaction temperature in the method according to the invention thus amounts to 80° C. to 130° C., preferably 100° C. to 120° C., and the reaction time is between 15 and 180 minutes, preferably between 30 and 120 minutes.

The catalyst is used in amounts of 0.001 mol to 0.05 mol, preferably in amounts of 0.005 mol to 0.03 mol, for each of alkali methacrylate or acrylate. The phase transfer catalysts to be used according to the invention are not stable at the temperature conditions as they are described in the examples of the Japanese application 51348/65; their thermal degradation above 140° C. is already considerable.

The reactants are generally used in a stoichiometric ratio. A slight excess of either the halogen alkylsilane or the alkali (meth)acrylate is possible, so that the molar ratio of the input alkali (meth)acrylate to the halogen silane can be between 1.2:1 and 1:1.2.

Preferably, the reaction is performed in the absence of additional solvents. It is also possible, however, to begin the reaction in the presence of organic anhydrous solvents (e.g., alcohols) which are introduced into the reaction system, for example, with one of the reactants. Such solvents, however, should then be substantially removed from the reaction mixture in the course of the reaction, preferably at the beginning of the reaction.

By avoiding large excesses of halogen alkylsilanes and by refraining from adding additional solvents in the reaction, there is no distillation of unused chloroalkylsilanes or solvents and both high yields per unit of space and time and a favorable energy balance are achieved.

The alkali methacrylates or alkali acrylates used according to the invention are the corresponding potassium or sodium salts. They can be introduced into the reaction vessel either as a solid, or a solution or dispersion in a suitable solvent. A preferred embodiment consists in using a methacrylate or acrylate which has been prepared by neutralizing methacrylic acid or acrylic acid with an alcoholic solution of a potassium alcoholate or sodium alcoholate. The solution or dispersion thus obtained is mixed with the halogen alkylsilane and the phase transfer catalyst. The alcohol is then distilled out. The reaction between the alkali methacrylate or acrylate and the halogen alkylsilane starts upon the removal of the alcohol.

Examples of halogen alkylsilanes of the general formula II which can be used according to the invention are chloromethyldimethylmethoxysilane;
γ-chloropropyltrimethoxysilane;
γ-chloropropyltriethoxysilane;
γ-chloropropyltris(methoxyethoxy)silane;
γ-chloropropylmethyldimethoxysilane;
γ-chloropropylbutyldimethoxysilane;
δ-chlorobutyltrimethoxysilane;
δ-chlorobutylmethyldimethoxysilane;
δ-chlorobutyltris(methoxyethoxy)silane; and
γ-bromopropyltrimethoxysilane.

The reaction of the alkali methacrylate or acrylate with a halogen alkylsilane of the general Formula II is performed by mixing the reactants and the phase transfer catalyst in the selected molar ratio. The reaction mixture thus obtained is then brought to the reaction temperature with constant stirring. Any additional solvent that may be present is at the same time distilled out.

Upon completion of the reaction, the formed acrylosilane is isolated in a known manner. It is desirable to distill out the acrylosilane, either after separating any precipitated alkali chloride, or directly from the resulting reaction mixture. It is generally desirable to perform the distillation under reduced pressure to protect the acrylosilane.

During the reaction it is advantageous to add known polymerization inhibitors to the reaction mixture. Suitable inhibitors include, for example, hydroquinone, hydroquinone monomethyl ether, N,N'-diphenyl-p-phenylenediamine, and phenyl-Δ-naphthylamine. The inhibitors are added in amounts of 0.001 to 1% of the weight of the acrylosilane. The distilled or otherwise isolated pure product is advantageously treated with the same inhibitors.

EXAMPLE 1

43 g (0.5 mol) of methacrylic acid is mixed with 45 g of methanol and the mixture is neutralized with 130 g of a 26.9% potassium methylate solution in methanol, with stirring. With continued stirring, 0.3 g of N,N'-diphenyl-p-phenylenediamine and 105.2 g (0.53 mol) of γ-chloropropyltrimethoxysilane are added drop by drop to the salt dispersion thus formed. At the same time methanol is distilled out, until the temperature of the mixture reaches 110° C. After cooling to 50° C., 1.7 g (0.004 mol) of ALIQUAT$^{(R)}$ 336 (commercial product of Henkel, Duesseldorf) is added and, after applying a vacuum the remaining methanol and 6 g (0.03 mol) of the γ-chloropropyltrimethoxysilane are distilled out.

The reaction mixture is maintained at 115° C. for 1.5 hours. Then it is cooled and the potassium chloride that has formed as by-product is filtered. The filtrate is distilled under reduced pressure. 114.5 g is obtained, of γ-(-methacryloxypropyltrimethoxysilane, b.p. 82° C. (0.4 mbar) and $n^{20}=1.4308$, which corresponds to a yield of 92.3% with respect to the methacrylic acid input.

EXAMPLE 2

54 g (0.5 mol) of solid sodium methacrylate is mixed with 99.3 g (0.5 mol) of γ-chloropropyltrimethoxysilane, 2.5 g (0.006 mol) of ALIQUAT$^{(R)}$ 336, and 0.4 g of N,N'-diphenyl-p-phenylenediamine and heated with stirring to 112° C. After 1 hour of reaction the mixture is cooled and the sodium chloride formed as byproduct is removed by filtration. The filtrate is distilled at reduced pressure and 119 g of γ-methacryloxypropyltrimethoxysilane, boiling point 82° C. (0.4 mbar) and $n^{20}=1.4308$ is obtained. With respect to the sodium methacrylate input, the yield amounts to 96.0%.

EXAMPLES 3 TO 6

In a variant of Example 1, the chloroalkylsilanes listed in the Table are used instead of γ-chloropropyltrimethoxysilane, with otherwise the same procedure as in Example 1. In the Table the yields and the boiling points of the corresponding methacryloxyslanes are listed.

TABLE

| Ex. | Chloroalkylsilane | grams | moles | Methacryloxysilane | Yield* grams | % | Boiling point °C./μbar |
|---|---|---|---|---|---|---|---|
| 3 | γ-chloropropyl-methyldimethoxy-silane | 93.2 | 0.51 | γ-methacryloxy-propylmethyldi-methoxysilane | 108.2 | 93.1 | 66/0.2 |
| 4 | γ-chloropropyl-triethoxysilane | 127.6 | 0.53 | γ-methacryloxy-propyltriethoxy-silane | 131.9 | 90.8 | 92/0.25 |
| 5 | δ-chlorobutyl-trimethoxysilane | 112.8 | 0.53 | δ-methacryloxy-butyltrimethoxy-silane | 120.0 | 91.5 | 82/0.13 |
| 6 | chloromethyl-dimethylmethoxy-silane | 77.6 | 0.56 | methacryloxymethyl-dimethylmethoxy-silane | 83.8 | 89.0 | 70/19.5 |

*with respect to 0.5 mol of input alkali methacrylate

EXAMPLE 7

55.1 g (0.5 mol) of potassium acrylate is mixed with 99.3 g (0.5 mol) of γ-chloropropyltrimethoxysilane, 3.75 g (0.008 mol) of ALIQUAT$^{(R)}$ 336 and 0.3 g of N,N-diphenyl-p-phenylenediamine and heated at 115° C. with stirring. After a reaction time of 1.5 hours the mixture is cooled and the potassium chloride that has formed as byproduct is filtered out. The filtrate is distilled under reduced pressure, whereupon 109.4 g of acryloxypropyltrimethoxysilane with a boiling point of 80° C. (0.5 mbar) is obtained. The yield amounts to 93.5% of the potassium acrylate put in.

EXAMPLE 8

In a modification of Example 1, 2.8 g (0.009 mol) of tetrabutylammonium bromide is used instead of ALIQUAT$^{(R)}$ 336, the procedure otherwise being the same as in Example 1. 112.5 g of γ-methacryloxypropyltrimethoxysilane is obtained, which corresponds to a yield of 90.7% with respect to the methacrylic acid put in.

EXAMPLE FOR COMPARISON

Example 1 is repeated, but instead of ALIQUAT$^{(R)}$ 336, trimethylbenzylammonium chloride is used as a quaternary ammonium salt, in an amount of 1.5 g (0.009 mol); otherwise the procedure is as in Example 1.

By distilling the filtrate under reduced pressure, 97.5 g of distillate was obtained with a boiling range of 60 to 86° C. (0.3 mbar). Gas-chromatographic analysis showed a content of 17.7 g of γ-methacryloxypropyl-trimethoxysilane, which corresponds to a yield of 14.3% with respect to the methacrylic acid input.

It will be understood that the specification and examples are illustrative but not limitative of the present invention and that other embodiments within the spirit and scope of the invention will suggest themselves to those skilled in the art.

We claim:

1. A method for the preparation of an organosilane containing a methacryloxy or an acryloxy group, of the general Formula I

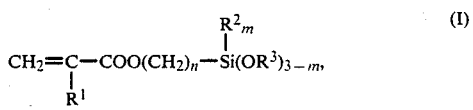

in which $R^1$ is a hydrogen atom or a methyl group, $R^2$ an alkyl moiety of 1 to 4 carbon atoms, $R^3$ an alkyl group with to 4 carbon atoms, or an alkoxyalkyl group with a total of 2 to 4 carbon atoms, m represents 0 or 1 or 2, and n represents 1, 3 or 4, comprising:

reacting at a temperature of from 80 to 130° C. an alkali methacrylate or acrylate with a halogen alkylsilane of the general Formula II

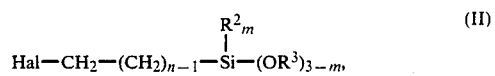

in which $R^2$, $R^3$, m and n are as defined above and Hal represents, chlorine or bromine, in the presence of a catalyst being a quaternary ammonium salt of the general Formula III

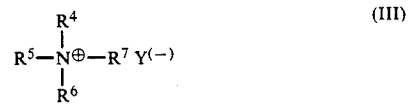

in which $Y^{(-)}$ is a halide ion, sulfate ion or phosphate ion and $R^4$, $R^5$, $R^6$ and $R^7$ are identical or different alkyl groups with 1 to 37 carbon atoms, the sum of all carbon atoms amounting to between 10 and 40.

2. The method of claim 1 wherein the quaternary ammonium salt is tris(n-$C_8$-and $C_{10}$-alkyl)methylammonium chloride.

3. The method of claim 1 wherein the reaction is performed in the absence of an additional solvent.

4. The method of claim 1 wherein the molar ratio of the input alkali methacrylate or acrylate to the halogen alkylsilane of Formula II is between 1.2:1 and 1:1.2.

5. The method of claim 1 wherein the reaction is conducted at a temperature of from 100 to 120° C.

6. The method of claim 1 wherein the catalyst is used in an amount of 0.001 to 0.05 mole per mole of alkali methacrylate or acrylate.

7. The method to claim 1 wherein the catalyst is used in an amount of 0.005 to 0.03 moles per mole of alkali methacrylate or acrylate.

8. The method of claim 1 wherein the catalyst is selected from one or more of the group consisting of tributyl methyl ammonium chloride, triethylcetyl ammonium bromide, didodecyl dimethyl ammonium chloride, distearyl dimethyl ammonium chloride, tricaprylmethyl ammonium chloride, ALIQUAT$^{(R)}$ 336 (tris(n-$C_8$-and $C_{10}$-alkyl)methyl ammonium chloride), trioctyl methyl ammonium chloride, tetrabutyl ammonium chloride or tetrabutyl ammonium bromide.

9. The method of claim 1 wherein the alkali methacrylate or alkali acrylate is a salt of sodium or potassium.

10. The method of claim 1 wherein the halogen alkylsilane is selected from the group consisting of chloromethyldimethylmethoxysilane,
γ-chloropropyltrimethoxysilane;
γ-chloropropyltriethoxysilane;
γ-chloropropyltris(methoxyethoxy)silane;
γ-chloropropylmethyldimethoxysilane;
γ-chloropropylbutyldimethoxysilane;
δ-chlorobutyltrimethoxysilane;
δ-chlorobutylmethyldimethoxysilane;
δ-chlorobutyltris(methoxyethoxy)silane; and
γ-bromopropyltrimethoxysilane.

11. The method of claim 1 wherein polymerization is inhibited by the addition of a polymerization inhibitor.

12. The method of claim 11 wherein the polymerization inhibitor is selected from the group consisting of hydroquinone, hydroquinone monomethyl ether, N,N'-diphenyl-p-phenylenediamine, and phenyl-α-naphthylamine.

13. The method of claim 11 wherein the polymerization inhibitor is used in an amount of 0.001 to 1 wt.-% of the organosilane of the Formula I.

14. The method of claim 1 wherein the methacrylate or acrylate is used in the form of a solution.

15. The method of claim 1 wherein the methacrylate or acrylate is used in the form of a dispersion.

* * * * *

UNITED STATES PATENT AND TRADEMARK OFFICE
CERTIFICATE OF CORRECTION

PATENT NO. : 4,946,977
DATED : August 7, 1990
INVENTOR(S) : Günther Bernhardt et al It is certified that error appears in the above-identified patent and that said Letters Patent is hereby corrected as shown below:

Column 4, line 20, " $\Delta$-naphthylamine" should read -- $\alpha$-naphthylamine--.

Column 5, last line, claim 1, "with to 4" should read --with 1 to 4--.

Signed and Sealed this

Twenty-third Day of March, 1993

Attest:

STEPHEN G. KUNIN

*Attesting Officer*     *Acting Commissioner of Patents and Trademarks*